United States Patent [19]

Kay et al.

[11] 3,982,132

[45] Sept. 21, 1976

[54] PATIENT RESTRAINING STRAP FOR SCINTIPHOTOGRAPHY

[75] Inventors: Thomas D. Kay; John W. Harper, both of San Antonio, Tex.

[73] Assignee: The United States of America as represented by the Secretary of the Air Force, Washington, D.C.

[22] Filed: Feb. 13, 1975

[21] Appl. No.: 550,110

[52] U.S. Cl. .......................... 250/456; 128/DIG. 20
[51] Int. Cl.² ................. G01N 21/00; G01N 23/00
[58] Field of Search .................. 250/491, 456, 439; 128/2.05 C, DIG. 20, DIG. 15

[56] References Cited
UNITED STATES PATENTS

| | | | |
|---|---|---|---|
| 3,224,415 | 12/1965 | Gottfried | 128/DIG. 20 |
| 3,358,141 | 12/1967 | Hoffmann et al. | 250/456 |
| 3,669,096 | 6/1972 | Hurwitz | 128/2.05 C |
| 3,752,148 | 8/1973 | Schmalzbach | 128/2.05 C |

*Primary Examiner*—Alfred E. Smith
*Assistant Examiner*—T. N. Grigsby
*Attorney, Agent, or Firm*—Joseph E. Rusz; Jacob N. Erlich

[57] ABSTRACT

A patient restraining strap for scintiphotography having a pair of expandable cloth-like bags joined together. The strap encompasses the head of a patient and is then secured to a Gamma Scintillation Camera. Once inflated the restraining strap immobilizes the head without discomfort to the patient during the scintiphotography procedure.

1 Claim, 1 Drawing Figure

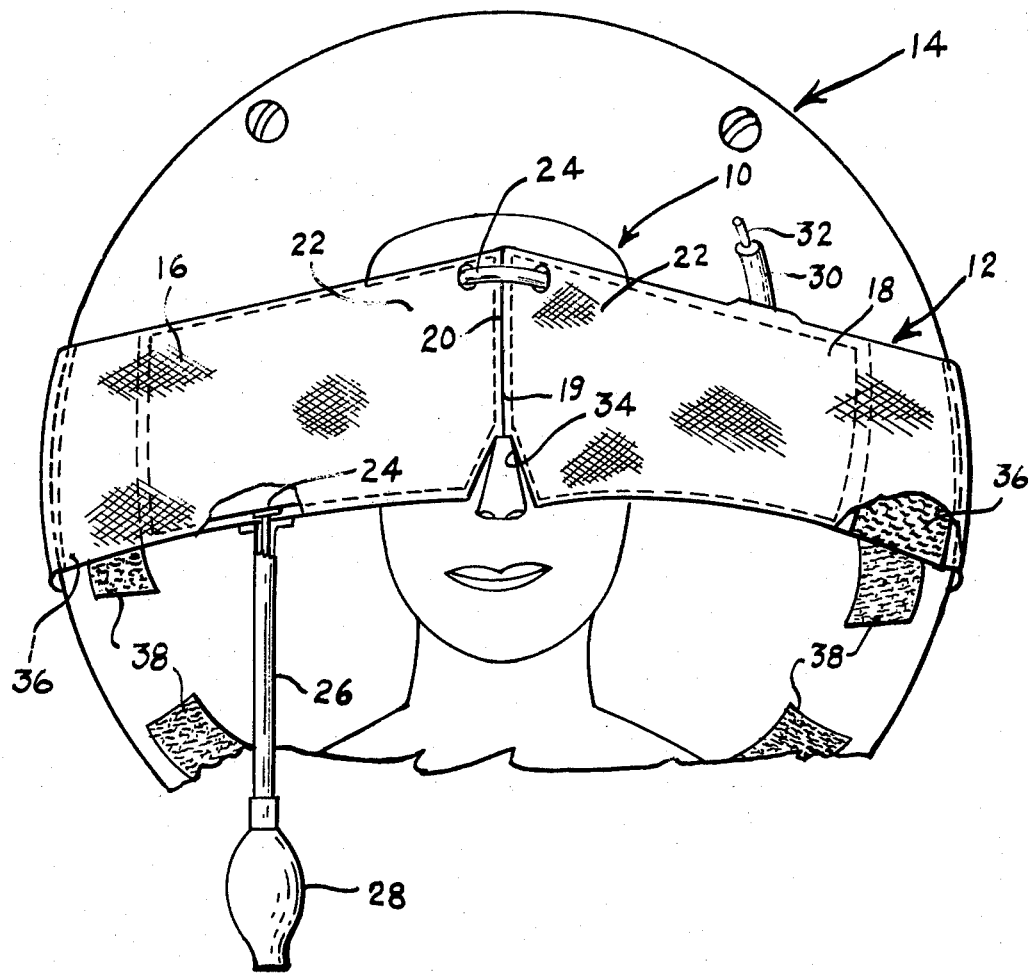

PATIENT RESTRAINING STRAP FOR SCINTIPHOTOGRAPHY

STATEMENT OF GOVERNMENT INTEREST

The invention described herein may be manufactured and used by or for the Government for govenmental purposes without the payment of any royalty thereon.

BACKGROUND OF THE INVENTION

This invention relates generally to scintiphotography, and, more particularly, to a restraining strap which is used with the Gamma Scintillation Camera during scintiphotography.

Scintiphotography is the diagnostic technique by which both normal and diseased organs within a patient can be studied by following the passage of radioisotopes through the organ. This procedure is performed by the use of a Gamma Scintillation Camera such as Nuclear Chicago's Pho/Gamma HP camera which has the ability to visualize the entire organ of interest at one time and to follow the passage of radioisotopes through the organ. Radiation from the radioisotope is rapidly detected and the position and intensity or the gamma events are produced and displayed in a corresponding position on a cathode ray tube display. Time exposures of the gamma image can be taken thereby providing studies of the organ function in both normal and diseased states. A choice of collimators for various resolution and sensitivity requirements help assure meaningful recordings for most clinical situations.

The Gamma Scintillation Camera System is made up of a gamma detector, assembly for supporting the detector and drive motors and controls for detector orientation. Within the gamma detector is a sodium-iodide thallium activated scintillation crystal. The control console is a desk type assembly which contains an XYZ Analyser, timer, display and power supply.

The counting time required to obtain an optional image of the emission distribution from a patient using a Gamma Scintillation camera is determined by the amount of the radioactivity administered, sensor sensitivity, lesion uptake and contrast ratio and the ability of the patient to remain still. The longer the time required for the study, the greater is the probability that significant motion artifacts will occur. Studies show that in organ scans the motion artifacts contribute to the deterioration of the quality of the image after a certain interval of time. For example, it has been found that image quality is good up to three minutes of the scan before motion artifacts reduce the useful information that can be obtained form the increased counting rate. Thus, in order to retain high diagnostic image quality in the longer duration studies, it is critical to devise improved patient restraining techniques. Heretofore, these restraining techniques were quite cumbersome in construction, uncomfortable to the patient, complicated in providing adjustability to a variety of shapes and sizes and produced gamma backscatter during the scintiphotography procedure.

SUMMARY OF THE INVENTION

The instant invention sets forth a patient restraining strap for scintiphotography with a Gamma Scintillation Camera which overcomes the problems set forth in detail hereinabove.

The restraining strap of this invention is in the form of a pair of bags made of any suitable cloth-like or fabric material. These bags are of a size sufficient to encompass the head of the patient under treatment. Within each bag is located an expandable bladder. A hand aspirator bulb or any suitable machine operated pump is connected to the bladders for expansion thereof during the restraining procedure.

A plurality of fastener elements are mounted at preselected points on the front of the scintillation camera. These fastener elements are used in conjunction with a plurality of fasteners mounted on the bags. As a result thereof the patient restraining device of this invention is capable of providing rapid adjustability and removability when in use. The expansion of the bladders holds the patient's head immobile with complete patient comfort during the scintiphotography operation.

It is therefore an object of this invention to provide a patient restraining device which is capable of use with the Gamma Scintillation Camera.

It is another object of this invention to provide a patient restraining device which does not contribute to an increase of gamma backscatter during scintiphotography.

It is a further object of this invention to provide a patient restraining device which can effectively immobilize the head of a patient with a minimum of patient discomfort.

It is still another object of this invention to provide a patient restraining device which is economical to produce and which utilizes conventional, currently available components that lend themselves to standard mass producing manufacturing techniques.

For a better understanding of the present invention together with other and further objects thereof reference is made to the following description taken in conjunction with the accompanying drawing and its scope will be pointed out in the appended claims.

DESCRIPTION OF THE DRAWING

The only FIGURE of the drawing is a pictorial representation, shown partly in cut-away section, of the patient restraining device of this invention in position on a Gamma Scintillation Camera and immobilizing the head of a patient undergoing treatment.

DETAILED DESCRIPTION OF THE PREFERRED EMBODIMENT

Reference is now made to the only FIGURE of the drawing which shows in pictorial fashion the head 10 of a patient being immobilized by the patient restraining strap 12 of this invention while undergoing treatment by a conventional Gamma Scintillation Camera 14.

Restraining strap 12 is made of a pair of elongated bags 16 and 18 secured together at 19 by any conventional securing technique such as heavy duty sewing. Bags 16 and 18 may be made of any cloth-like or fabric material such as canvas. Contained within each bag 16 and 18 is a suitable resilient, expandable bladder 22 made of, for example, rubber. Bladders 22 are joined to each other by any suitable connecting means such as hose 24. One of the bladders 22 has attached thereto an air-intake pipe 24, hose 26 and an aspirator bulb 28, or any suitable air pump (not shown). The other bag 22 has attached thereto an air outlet 30 and any conventional plug 32. Plug 32 is removed when it is desired to evacuate bladders 22 after the restraining procedure has been completed.

Bags 16 and 18 have a combined cutout portion 34 so that the nose of the patient 10 may protrude therethrough during the restraining procedure. In addition, bags 16 and 18 have located on the interior surface thereof at each end thereof any suitable quick release fastening element 36 which may take the form of a Valco tape. A plurality of mating fasteners 38 are secured at various points along the head of the camera 14 for proper positioning of the restraining strap 12 of this invention. These fasteners 38 may also be in the form of Valco tapes.

Once the patient 10 is positioned against the scintillation camera 14, the deflated restraining strap 12 of this invention is placed against the forehead of patient 10 and secured by means of fasteners 36 and 38 to camera 14. In position, bladders 22 of restraining strap 12 are inflated by means of aspirator bulb 28 until the head of patient 10 is completely immobilized in the desired position. In this position the scintiphotography operation can commence for the desired period of time with the patient being completely stationary and having no discomfort whatsoever. There is no metal used with the restraining strap of this invention and therefore any Gamma backscatter has been eliminated.

Although this invention has been described with reference to a particular embodiment it will be understood to those skilled in the art that this invention is also capable of a variety of alternate embodiments within the spirit and scope of the appended claims.

We claim:

1. The combination of a patient restraining strap and scintillation camera comprising a plurality of fastening elements secured in preselected locations to said camera, said restraining strap being formed of a body having an elongated configuration, fastening means located on the interior portion of said body for removable and adjustable attachment to said fastening elements on said camera, said body being in the form of a pair of cloth-like bags connected together in side-by-side relationship along the longitudinal dimension of said body, each of said bags containing a resilient expandable bladder therein, a pipe interconnecting said bladders, means connected to one of said bladders for expanding said bladders, means connected to the other of said bladders for deflating said bladders and a cutout portion located at the connection of said bags for allowing the nose of a patient to protrude therethrough whereby said restraining strap, when expanded, comfortably immobilizes against said camera the head of a patient undergoing treatment by said scintillation camera.

* * * * *